US008005947B2

(12) United States Patent  (10) Patent No.: US 8,005,947 B2
Morris et al.  (45) Date of Patent: Aug. 23, 2011

(54) SYSTEMS AND METHODS FOR PROVIDING REMOTE DIAGNOSTICS AND SUPPORT FOR SURGICAL SYSTEMS (75) Inventors: Wes Morris, Aliso Viejo, CA (US); Robert V. Loschy, Lake Forest, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 332 days.

(21) Appl. No.: 12/235,375

(22) Filed: Sep. 22, 2008

(65) Prior Publication Data
US 2010/0076453 A1 Mar. 25, 2010

(51) Int. Cl.
G06F 15/173 (2006.01)
A61B 19/00 (2006.01)
(52) U.S. Cl. .................................. 709/224; 606/130
(58) Field of Classification Search .............. 709/224; 606/130
See application file for complete search history.

(56) References Cited

U.S. PATENT DOCUMENTS

| | | | |
|---|---|---|---|
| 6,149,643 A * | 11/2000 | Herekar et al. ................. 606/5 |
| 6,648,223 B2 * | 11/2003 | Boukhny et al. ............... 235/385 |
| 7,027,233 B2 * | 4/2006 | Goldstein et al. ............. 359/697 |
| 2002/0032470 A1 * | 3/2002 | Linberg ........................... 607/60 |
| 2002/0082665 A1 * | 6/2002 | Haller et al. ..................... 607/60 |
| 2003/0178489 A1 * | 9/2003 | Boukhny et al. ........... 235/462.13 |
| 2004/0073403 A1 * | 4/2004 | Hart et al. ....................... 702/183 |
| 2005/0187838 A1 * | 8/2005 | Squeglia et al. .................. 705/29 |
| 2006/0025670 A1 * | 2/2006 | Kim et al. ........................ 600/407 |
| 2006/0274794 A1 | 12/2006 | Watanabe et al. |
| 2007/0124737 A1 * | 5/2007 | Wensley et al. ................. 719/314 |
| 2007/0135866 A1 * | 6/2007 | Baker et al. ...................... 607/60 |
| 2007/0255114 A1 * | 11/2007 | Ackermann et al. .......... 600/300 |
| 2008/0082661 A1 * | 4/2008 | Huber ............................. 709/224 |
| 2008/0109051 A1 * | 5/2008 | Splinter et al. .................. 607/60 |
| 2008/0122407 A1 * | 5/2008 | Khashayar ..................... 320/166 |
| 2008/0197194 A1 * | 8/2008 | Flood ............................. 235/385 |
| 2008/0281254 A1 * | 11/2008 | Humayun et al. ............... 604/22 |
| 2008/0315829 A1 * | 12/2008 | Jones et al. .................... 320/103 |
| 2009/0012374 A1 * | 1/2009 | Schmelzeisen-Redeker et al. ............................. 600/301 |
| 2009/0227876 A1 * | 9/2009 | Tran ............................... 600/483 |
| 2009/0257024 A1 * | 10/2009 | Luther et al. ................... 351/206 |
| 2009/0300507 A1 * | 12/2009 | Raghavan et al. ............. 715/738 |
| 2009/0312052 A1 * | 12/2009 | Barbosa et al. ............. 455/556.1 |

FOREIGN PATENT DOCUMENTS

| | | | |
|---|---|---|---|
| WO | WO0148676 A1 | 7/2001 |
| WO | WO02068047 A2 | 9/2002 |
| WO | WO2008098299 A1 | 8/2008 |

* cited by examiner

*Primary Examiner* — Alina N. Boutah (57) ABSTRACT

Systems and methods for medical care, and more particularly, systems and methods for providing remote diagnostics and support for surgical systems. A central computer system is communicatively coupled to one or more computer-based surgical machines. The central computer system is programmed to monitor the operation of each of the surgical machines, diagnose any problems that occur with the machines, and notify a technician of potential problems with the machines to provide for an efficient support system that minimizes undesirable downtime of the surgical machines.

14 Claims, 5 Drawing Sheets

SYSTEMS AND METHODS FOR PROVIDING REMOTE DIAGNOSTICS AND SUPPORT FOR SURGICAL SYSTEMS

FIELD OF THE INVENTION

The field of the invention relates to systems and methods for medical care, and more particularly to systems and methods for providing remote diagnostics and support for surgical systems.

BACKGROUND OF THE INVENTION

Figure 1A:
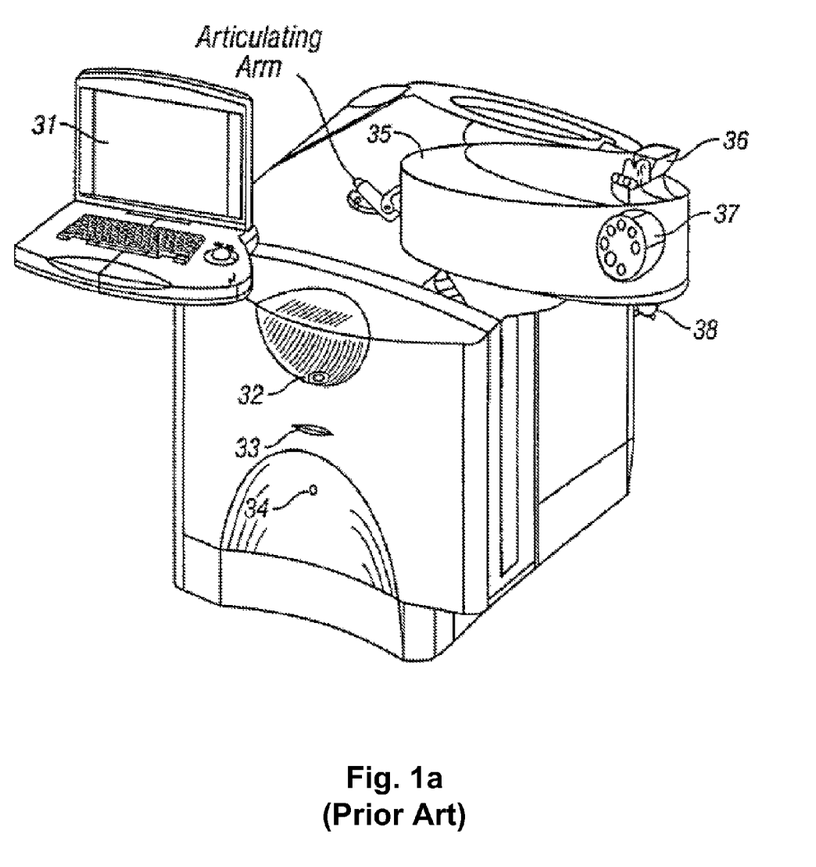
FIG. 1a is a perspective view of an ophthalmic laser system known in the art.
Figure 1B:
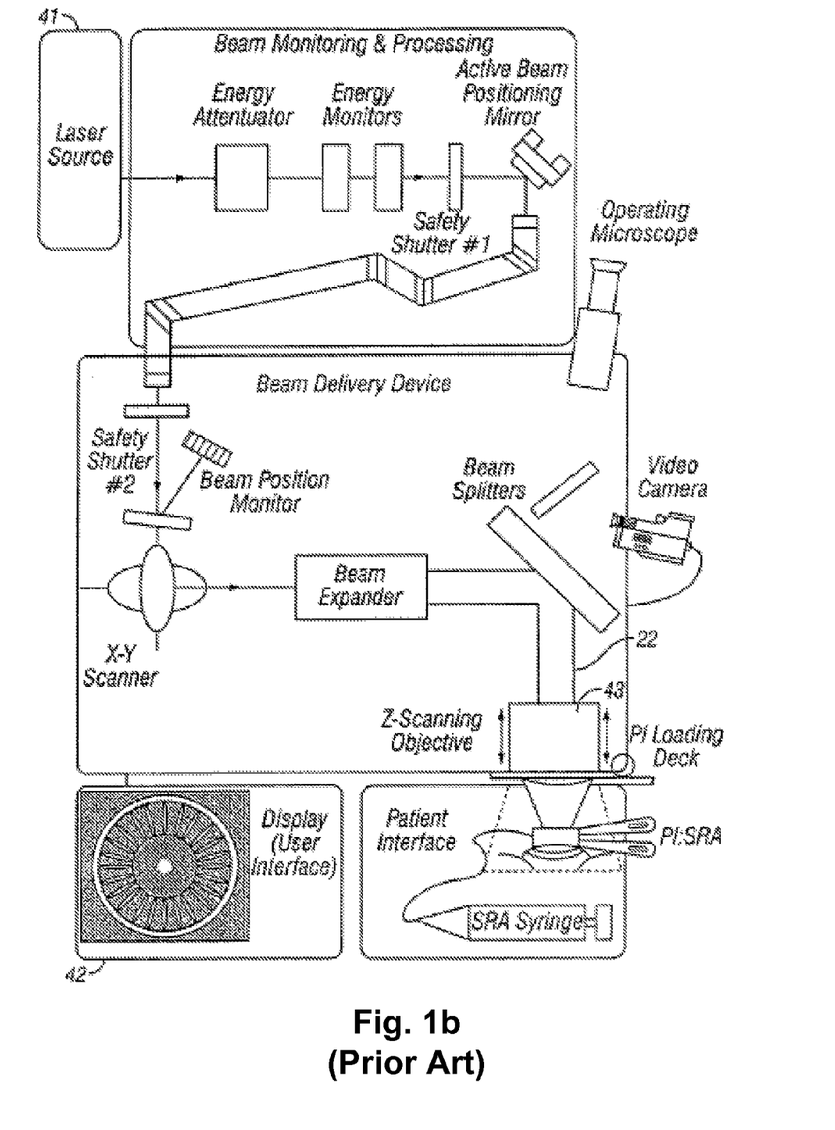

A surgical system typically has a large and complex set of inter-operating components, each contributing to the proper operation of the system. For example, an exemplary ophthalmic laser system is shown in FIGS. 1a and 1b, which includes a number of electronic and mechanical parts. FIG. 1a is a perspective view of the exemplary ophthalmic laser system. In this example, a user interface and terminal 31 provides for data input into a CPU (not shown) of desired focal values for the laser. The system further includes an emergency shut off switch 32, disk drive 33 key switch 34, beam delivery device 35, operating microscope 36, control panel 37, and a loading deck 38 for interface with an eye-stabilizing device.

Referring to FIG. 1b, a block diagram of the exemplary ophthalmic laser system of FIG. 1a is shown. A laser source 41 is directed through a beam delivery device into a z-scanning objective lens 43 via path 22. A display 42 is provided for viewing the eye undergoing laser treatment. In general, the operation of the system may be in accordance with the disclosure of U.S. Pat. No. 7,027,233, which is incorporated herein in entirety by reference.

Figure 2:
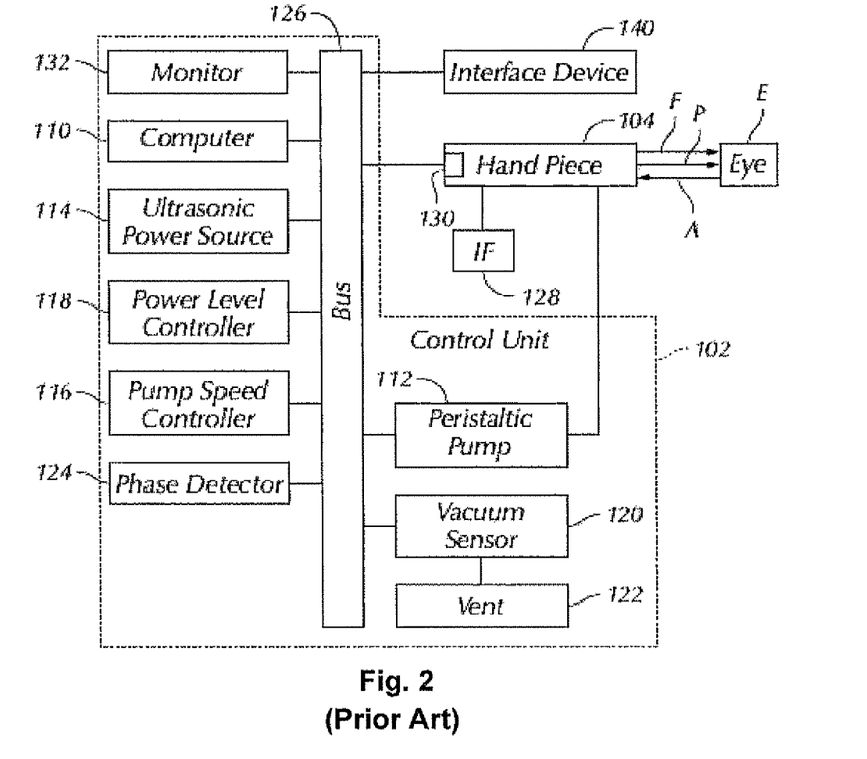
FIG. 2 is a block diagram of a phacoemulsification system known in the art.
Figure 3:
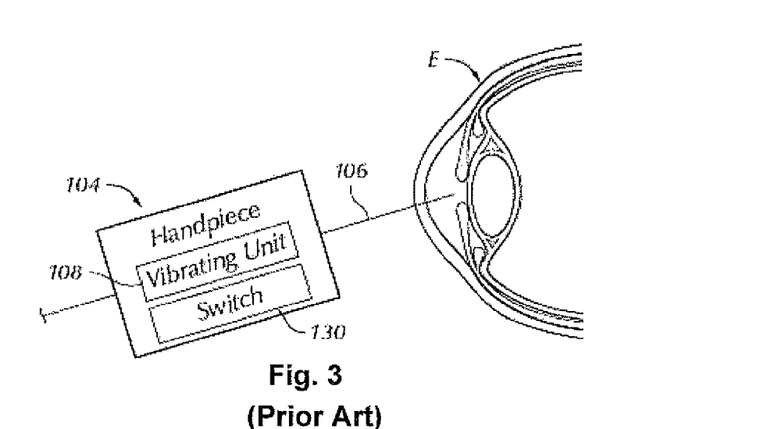
FIG. 3 is a block diagram illustrating a handpiece for a phacoemulsficiation system known in the art.

Another complex surgical system is a phacoemulsification system, which removes the lens of an eye (e.g., following impairment by cataract). Turning to FIG. 2, a block diagram of a phacoemulsification system 100 known in the art is shown. The system 100 includes a control unit 102 and a handpiece 104 operably coupled together. FIG. 3 is a block diagram illustrating the handpiece 104. As shown in FIG. 3, the handpiece 104 includes a needle 106 for insertion into an eye E and a vibrating unit 108 that is configured to ultrasonically vibrate the needle 106. The vibrating unit 108, which may operate using a piezoelectric crystal, for example, vibrates the needle 106 based on one or more parameters, such as frequency, pulse width, shape, size, duty cycle, amplitude, and so on.

The phacoemulsification system 100 includes a microprocessor computer 110 that is operably connected to and controls a number of other elements of the system 100. In some embodiments, the system 100 includes a variable speed pump 112 (e.g., a peristaltic and/or venturi pump, and the like) to provide a vacuum source, a pulsed ultrasonic power source 114, a pump speed controller 16, and an ultrasonic power level controller 118. A vacuum sensor 120 provides an input signal to the computer 110 representing the vacuum level on the output side of the pump 112. Venting may be provided by a vent 122. The system 100 may also include a phase detector 124 to provide an input to the computer 100 that represents a phase shift between a sine wave representation of the voltage applied to the handpiece 104 and the resultant current into the handpiece 104. The functional representation of the system 100 also includes a system bus 126 that enables the various elements to operably communicate with each other.

In operation, the control unit 102 supplies ultrasonic power to the phacoemulsification handpiece 104. An irrigation fluid source 128 provides irrigation fluid to the handpiece 104. The irrigation fluid and an ultrasonic pulse are applied by the handpiece 104 to a patient's eye E, which are indicated by arrows F and P, respectively. Aspiration of the eye E is achieved by the pump 112, which is indicated by arrow A. The handpiece 104 may include a switch 130 for enabling a surgeon to select an amplitude of electrical pulses to the handpiece 104 via the computer 110, the power level controller 118, and the ultrasonic power source 114. The operation of the system 100 in general may be in accordance with the disclosure of U.S. Pat. No. 6,629,948, which is incorporated herein in entirety by reference.

For any of these systems, a failure of any one of these components could disable the operation of the entire system. However, fail-safe mechanisms are typically deployed with these systems to de-activate the corresponding component(s) and/or indicate a service alert in the event an improper operating status is detected. In response to the alert, a service technician is dispatched to diagnose the system. However, contacting the technician and waiting for the technician to arrive generally increases system downtime, prevents treatment of patients, and substantially increases costs to the system owner. One approach has been to provide preventative maintenance on a scheduled routine basis. This, however can create unnecessary service visits, particularly when the preventative maintenance schedule does not correlate with actual system performance and needs. Moreover, once one or more components, or the entire system, have been de-activated, the accessible information is generally insufficient for proper diagnosis. Accordingly, improved systems and methods for diagnosing and supporting surgical systems to reduce system downtime are desirable.

SUMMARY OF THE INVENTION

The invention is generally directed to systems and methods for medical care, and more particularly to systems and methods for providing remote diagnostics and support for surgical systems. The invention includes a central computer system communicatively coupled to one or more computer-based surgical machines via a computer network, such as the Internet. The central computer system is programmed to monitor the operation of one or more of the surgical machines, diagnose any problems that occur with one or more of the machines, and notify a technician of any potential problems with any of the machines to provide for an efficient support system that minimizes any potential undesirable downtime of the surgical machines.

In one embodiment, a service system for supporting ophthalmic surgical systems is provided. The service system includes a plurality of remotely located ophthalmic surgical machines, a plurality of personal digital assistants, and a central computer system communicatively coupled to each of the plurality of ophthalmic surgical machines and to each of the plurality of personal digital assistant. The central computer system is configured to detect an operation fault of at least one of the plurality of ophthalmic surgical machines and notify at least one of the personal digital assistants of the operation fault. The operation fault indicates a service requirement of the ophthalmic surgical machine.

In another embodiment, a method of servicing a plurality of surgical systems is provided. The method includes monitoring the plurality of surgical systems to obtain data indicating a status for each of the plurality of surgical systems, determining an operation fault of at least one surgical system of the plurality of surgical systems based on the data and a database of pre-determined profiles corresponding to each of the plurality of surgical systems, and notifying at least one technician of the operation fault.

In yet another embodiment, a support system for a plurality of remotely located ophthalmic surgical machines is provided. The support system includes a plurality of personal digital assistants and a central computer system communicatively coupled to each of the plurality of ophthalmic surgical machines and to each of the plurality of personal digital assistants. The central computer system is configured to receive data from at least one of the plurality of ophthalmic surgical machines, detect an operation fault of at least one of the plurality of ophthalmic surgical machines based on the data and a database on profiles corresponding to each of the plurality of ophthalmic surgical machines, and transmit an alert to at least one of the personal digital assistants. The operation fault indicates a service requirement of the ophthalmic surgical machine, and the alert indicates the operation fault.

Other systems, methods, features and advantages of the invention will be or will become apparent to one with skill in the art upon examination of the following figures and detailed description. It is intended that all such additional systems, methods, features mid advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 1b is as a block diagram of the ophthalmic laser system shown in FIG. 1a.

DETAILED DESCRIPTION OF THE PREFERRED EMBODIMENTS

Figure 4:
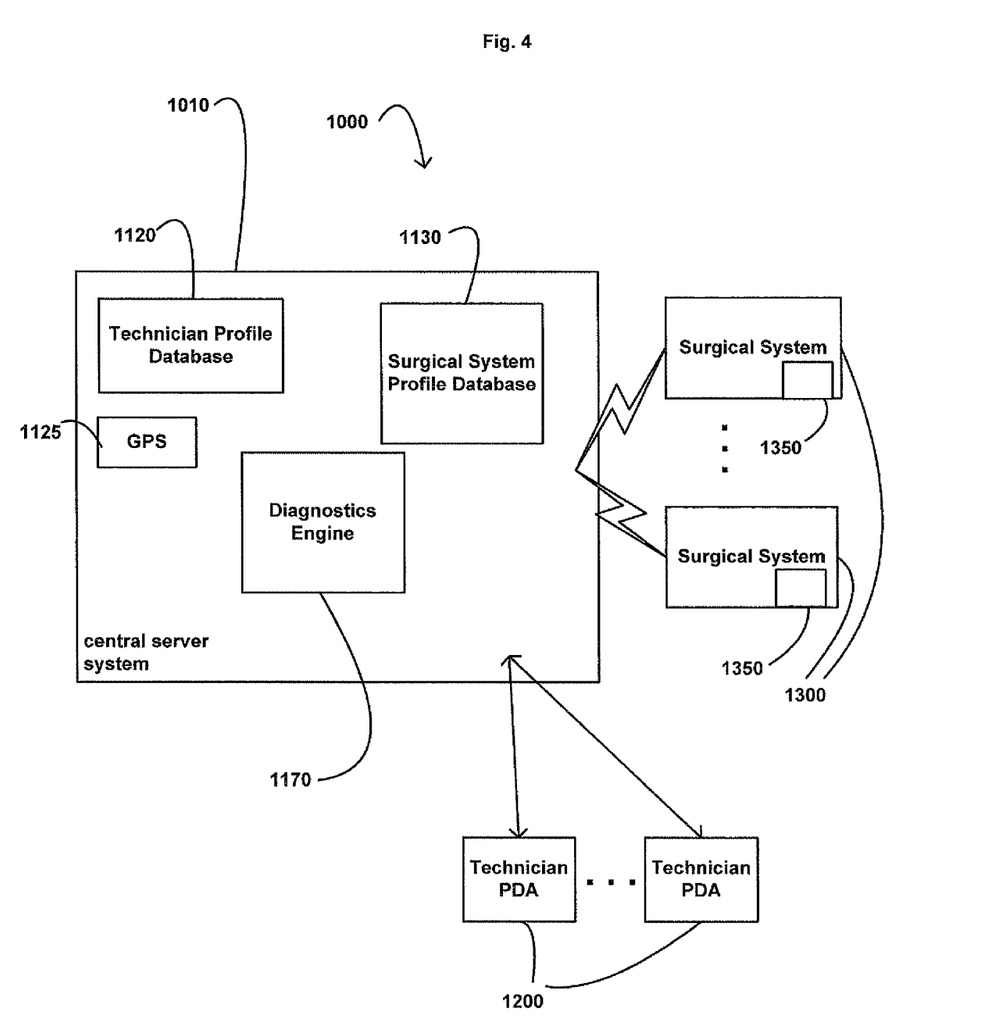
FIG. 4 is a diagram of a system in accordance with a preferred embodiment of the present invention.

Referring to the drawings, a computer-based diagnostics system 1000 is shown in FIG. 4 for monitoring, diagnosing, calibrating, and supporting surgical systems 1300 to reduce the downtime of the surgical system 1300. The system 1000 includes, but is not necessarily limited to, a central server system 1010 and one or more personal digital assistants ("PDAs") 1200. The central server system 1010 transmits and receives system diagnostics related information to and from, respectively, various surgical systems 1300 (e.g., ophthalmic based surgical systems such as those described above) via a network connection, such as the Internet (such network connectivity can include a combination of wide area networks, local area networks, interconnected networks, extranets, and intranets and can include devices such as routers, switches, and network interface cards). The surgical systems 1300 may be remotely located at one or more surgical centers and hospitals over a wide region (e.g., globally or the like).

In one embodiment, each surgical system 1300 includes a computer-based monitoring subsystem 1350 known in the art (e.g., a controller or a processor and a data storage device, such as a memory) that is configured to monitor various aspects of components critical to the operation of the surgical system 1300, although non-critical components may also be monitored. The monitoring subsystem 1350 collects the diagnostics related information for transmission to the central server system 1010. The PDAs 1200 are used by field technicians who can travel to the various surgical systems 1300 to resolve any problems, and the PDAs 1200 transmit and receive diagnostics related information specific to the corresponding surgical system 1300 to and from, respectively, the central server system 1010 and/or the various surgical systems 1300. The PDAs 1200 may include, by way of example and not limitation, to laptop computers, cell phones, or other portable wireless computing devices with network capabilities.

The central server system 1010 further includes a database of profiles 1130 associated with each monitored surgical system 1300. The surgical system database 1130 stores information about each surgical system 1300, e.g., type of system 1300 (e.g., an excimer laser, a femtosecond laser, and/or an ultrasound system), model, account information, owner, schedule of surgeries, surgeons approved to use the system 1300, location, usage history, diagnostics information, such as error logs and service history, and the like. Some fields are described below and based upon the type of surgical system 1300.

The central server system 1010 also includes a database 1120 of technician profiles that stores information about various technicians, e.g., location, schedule, completed service requests, time of completion, outstanding service requests, initiation time of service requests (e.g., to gauge quality of service), and the like. The server system 1010 can further include a global positioning system module 1125 that locates technicians based on the respective PDA 1200 to determine if a particular technician within a pre-determined vicinity of a surgical system 1300 requiring service or repair.

The central server system 1010 can provide a user interface (not shown) in the form of a webpage for convenient access and control of the central server system 1010 and the surgical systems 1300. In one embodiment, the interface includes a dashboard that is updated in real-time with the most current information about the surgical systems 1300. This dashboard can be configurable by the user and incorporate parameters from other business metrics to manage resources, cost, quality, and the like. The central server system 1010 can further include configuration management systems such as those described in U.S. patent application Ser. No. 11/839,074, which is hereby incorporated by reference in entirety.

Another component included in the central server system 1010 is a surgical system diagnostics engine 1170. This engine 1170 receives diagnostics related data from the various surgical systems 1300 and the surgical system profile database 1130 to determine the operating status of one or more components for a particular system 1300 or to receive an alert from a particular surgical system 1300 indicating the status of one or more components of the particular surgical system 1300 (e.g., a problem has occurred with one or more components of the particular surgical system 1300). This engine 1170 includes a computer-based algorithm tailored to diagnosing one or more types of surgical systems 1300, e.g., an excimer laser, a femtosecond laser, a cataract removal system, and the like. The central server 1010 can also include a number of computer servers located throughout different locations (e.g., across the world) to provide redundancy and reduce latency, as one of ordinary skill in the art would appreciate.

Figure 5:
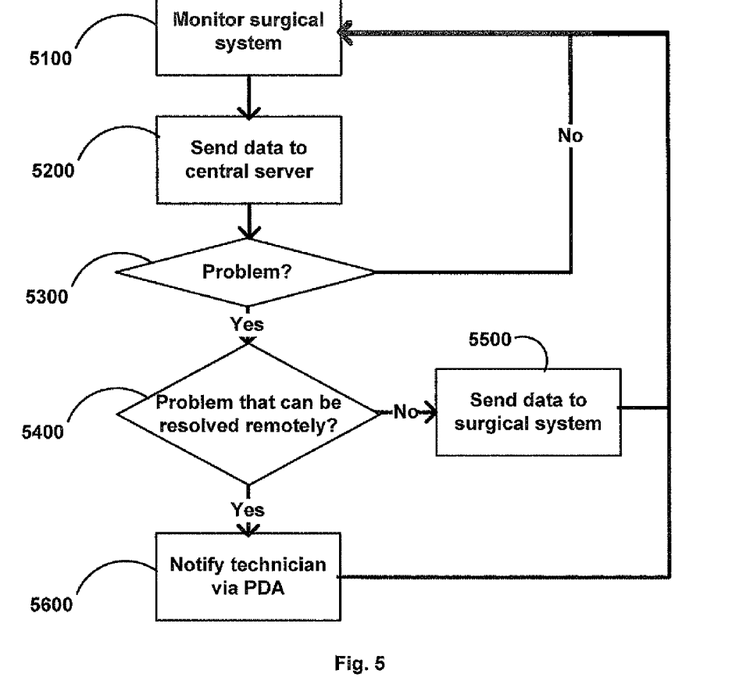
FIG. 5 is a flow diagram showing the operation of a system in accordance with a preferred embodiment of the invention.

FIG. 5 is a flow diagram of a method of remote diagnosing one or more surgical systems. During operation, referring to FIGS. 4 and 5, the various surgical systems 1300 are monitored (e.g., periodically or otherwise), as indicated at 5100. For example, the surgical systems 1300 can self-monitor for alerts or faulty operating conditions of components. Diagnostic related information is collected and sent to the central server 1010, e.g., via the monitoring subsystem 1350 as indicated at 5200. The diagnostic related information is evaluated to detect an operation fault of the surgical system 1300, as indicated at 5300. For example, the central server 1010, via the diagnostics engine 1170, the surgical system 1300, or both can detect an operation fault. If no operation fault is detected, the surgical systems 1300 continue to be monitored, as indicated at 5100. If an operation fault is detected, then a determination is made as to a remote resolution of the operation fault, as indicated at 5400. If the operation fault can be resolved remotely (e.g., away from the surgical system 1300 at a customer site), then the relevant data for remote resolution is transmitted to the surgical system 1300 indicating the operation fault, as indicated at 5500, and the surgical systems 1300 continue to be monitored, as indicated at 5100. For example, in the event a software upgrade, patch, updated configuration file(s), updated calibration data, or the like may be used to remotely resolve the operation fault, the central server 1010 transmits the same to the surgical system 1300, indicating the operation fault, over the remote network. If the operation fault cannot be resolved remotely, then a technician is notified via the PDA 1200, as indicated at 5600. For example, in the event the operation fault requires the personal attention of a technician, the central server system 1010 or the surgical system 1300 notifies a nearby technician, via the PDA 1200, of the operation fault and transmits information that may be used to resolve the problem (e.g., the technician can equip with the appropriate tools and/or replacement parts for visiting the site of the surgical system 1300 based on this information). The technician may also remotely access the surgical system 1300 to correct the operation fault, if possible. For example, if the system 1300 needs a software or configuration upgrade/update, the technician may be able to remotely initiate this via the central server 1010 through the technician's PDA 1200 without the need for a visit to the customer site. The service provided by the technician and/or the diagnostics system 1000 can be viewable and tracked by the customer/owner of the surgical system 1300 being serviced via a website (not shown).

In another embodiment, some operation faults may be categorized for technician attention, regardless of the ability to remotely correct the operation fault. In these cases, the operation fault is compared with a pre-determined database of operation faults categorized for technician attention, instead of determining the remote resolution. A variety of factors may be used to establish this database, such as historical experience, industry standards, operating capacity buffers or margins, and the like, although any parameter that would degrade over time may be monitored.

Figure 6:
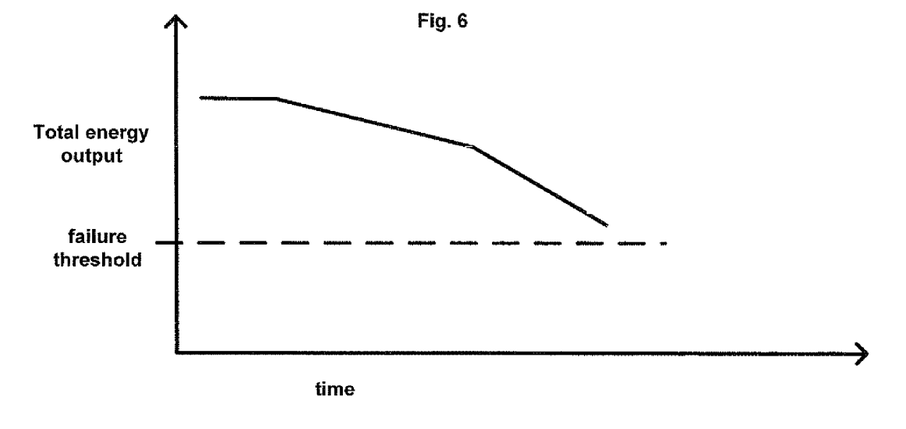
FIG. 6 is a graph illustrating the operation of a system in accordance with a preferred embodiment of the invention.

For an ophthalmic laser system 1300, e.g., a femtosecond laser known in the art (such as that shown in FIGS. 1a and 1b), the laser system 1300 generates a total output of surgical laser energy. During normal operation, the total output can slowly decline over time, as illustrated in FIG. 6. In one aspect of a preferred embodiment of the present invention, a monitoring subsystem (not shown), residing in the surgical system 1300 and/or the central server system 1010, periodically measures and stores the total output of surgical laser energy over time for the various laser systems 1300 (e.g., in an energy history log, which can be stored in the corresponding surgical system profile database 1130). Preferably, the measurement is performed at system power-up and then periodically during operation (e.g., on an hourly basis throughout a day of operation, on a monthly basis, and the like). The monitoring subsystem 1350 collects these measurements as data points, and a predicted service period (e.g., based on a pre-determined algorithm) can be calculated by the diagnostics engine 1170 or the surgical system itself 1300. This predicted service period indicates, for example, a probable occurrence of a component failure, a standardized replacement life of the component, and the like. In one embodiment, a threshold (e.g., a minimum total energy output corresponding with a desired photoalteration effect or the like) is used to approximate the service period. This service period is then stored in the surgical system profile database 1130 and forwarded to one or more PDAs 1200, each associated with an available or appropriate technician. A service visit can then be scheduled in advance of the predicted service period, and the technician can verify the output energy levels and service the laser system 1300 (e.g., to prevent a predicted failure and any possible downtime associated therewith).

For example, the service visit may include adjusting mirror positions, diode power, or other electrical settings to increase the output energy level from a predicted or detected decrease. In addition, the slope of the data points over time can be determined, either by the surgical system 1300 or the diagnostics engine 1170, to indicate a decline, change, or normal rate of the total energy output. For example, in the event the slope of the total energy output is steeper than a pre-determined threshold rate, the technician is notified of the operation fault of the surgical system 1300. Technician attention can thus be expedited to resolve an operation fault that may be indicative of a potential problem other than normal wear, for example, a failure of a component within the optical path of the laser. Other aspects of the laser surgical system 1300 that can be monitored, verified, and/or calibrated utilizing the diagnostics system 1000 include, but are not necessarily limited to, beam steering error, coolant level error, shutter error, laser diode error, galvo positioning error, energy sensors, wavefront measurements, voltage measurements, and the like. History logs for each of these aspects of the laser surgical system 1300 can be stored in the surgical profile database 1130 and used to predict the operation or performance status of the system 1300 (e.g., predict when performance of one or more corresponding components of the system 1300 degrades beyond the pre-determined threshold level).

For a phacoemulsification surgical system 1300, such as shown in FIG. 2, various components can be monitored via the monitoring subsystem 1350. For example, a peristaltic or flow-based aspiration pump 112 typically utilizes a rotary vain pump, which may wear over time. The monitoring subsystem 1350 logs the amount of time that the pump 112 is used. Once a use threshold is reached, the central server system 1300 transmits an alert to a nearby technician indicating that the pump 112 needs service (e.g., replacement), and can order a replacement pump for delivery to the surgical system 1300 site in advance of the technician's arrival for efficient service. Other aspects of the phacoemulsification system 1300 that can be monitored include the amount of time for the system to prime, vacuum performance, power performance, and the like. Additionally, power error, temperature error, computer error, safety error, footswitch or footpedal error, account warranty status, and the serial and lot numbers of the various components of the system 1300 can also be monitored. History logs for each of these aspects of the phacoemulsification surgical system 1300 can be stored in the surgical profile database 1130 and used to predict the operation or performance status of the system 1300 (e.g., predict when performance of one or more corresponding components of the system 1300 degrades beyond the pre-determined threshold level).

In one embodiment, the diagnostics system 1000 is combined with an inventory management system, where the surgical system profile database 1130 can further include surgery schedules, required inventory for a particular surgery, patient surgery information, and the like. An example system is described in U.S. Patent Application No. 61/005,459, filed Dec. 3, 2007, which is hereby incorporated in entirety by reference.

In the foregoing specification, the invention has been described with reference to specific embodiments thereof. It will, however, be evident that various modifications and changes may be made thereto without departing from the broader spirit and scope of the invention. For example, the specific ordering and combination of process actions described herein is merely illustrative, and the invention may appropriately be performed using different or additional process actions, or a different combination or ordering of process actions. For example, this invention is particularly suited for applications involving medical systems, but can be used beyond medical systems in general. As a further example, each feature of one embodiment can be mixed and matched with other features shown in other embodiments. Additionally, and obviously, features may be added or subtracted as desired. Accordingly, the invention is not to be restricted except in light of the attached claims and equivalents thereof.

What is claimed is:

1. A service system for supporting ophthalmic surgical systems, the service system comprising: a plurality of remotely located ophthalmic surgical machines each configured to transmit diagnostics data;
 a plurality of personal digital assistants; and
 a central computer system comprising a network connection communicatively coupled to each of the plurality of ophthalmic surgical machines and to each of the plurality of personal digital assistant, the central computer system further comprising a database of system profiles associated with each of the ophthalmic surgical machines, a database of technician profiles associated with each of the personal digital assistants, and a diagnostics engine configured to receive the diagnostics data from the ophthalmic surgical machines, the diagnostics engine including a computer-based algorithm configured to:
 detect an operation fault of at least one of the plurality of ophthalmic surgical machines based on the diagnostics data and the database of system profiles, the operation fault indicating a service requirement of the at least one of the plurality of ophthalmic surgical machines; and
 notify at least one of the personal digital assistants of the operation fault using the database of technician profiles.

2. The service system of claim 1, wherein the central computer system is configured to send software upgrades to any of the ophthalmic surgical machines upon receiving a request.

3. The service system of claim 1, wherein the plurality of ophthalmic surgical machines comprises one or more ophthalmic laser surgical machines, each of the one or more ophthalmic laser surgical machines configured to produce a total output energy amount during operation; and wherein the central computer system is further configured to:
 monitor the total output energy amount of each of the one or more ophthalmic laser surgical machines; and
 detect the operation fault when the total output energy amount of at least one of the one or more ophthalmic laser surgical machines exceeds a threshold energy level.

4. The service system of claim 3, wherein the central computer system comprises a database of profiles for each of the one or more ophthalmic laser surgical machines, the database of profiles based on at least one of the total output energy amount of each of the one or more ophthalmic laser surgical machines, a beam steering error, a coolant level error, a shutter error, a laser diode error, a galvo positioning error, a wavefront measurement, and a voltage measurement, and wherein the central computer system is further configured to predict the service requirement using the database of profiles.

5. The service system of claim 3, wherein the central computer system is further configured to:
 determine a rate of change of the total output energy amount of each of the one or more ophthalmic laser surgical machines; and
 detect the operation fault when the rate of change of the total output energy amount of at least one of the one or more ophthalmic laser surgical machines exceeds a threshold rate.

6. The service system of claim 1, wherein the plurality of ophthalmic surgical machines comprises one or more phacoemulsification machines, each of the one or more phacoemulsification machines having a rotary vain pump, and wherein the central computer system is further configured to:
 monitor a total usage of the rotary vain pump of each of the one or more phacoemulsification machines; and
 detect the operation fault when the total usage of the rotary vain pump of at least one of the one or more phacoemulsification machines exceeds a threshold value.

7. The service system of claim 6 wherein the database of system profiles comprises a database of system profiles for each of the one or more phacoemulsification machines, the database of system profiles for each of the one or more phacoemulsification machines based on at least one of the total usage of the rotary vain pump of each of the one or more phacoemulsification machines, an amount of time for priming, a vacuum performance, a power performance, a power error, a temperature error, a computer error, a safety error, a footswitch error, an account warranty status, and a serial/lot number, and wherein the central computer system is further configured to predict the service requirement using the database of system profiles.

8. A support system for a plurality of remotely located ophthalmic surgical machines, the support system comprising:
 a plurality of personal digital assistants; and
 a central computer system comprising a network connection communicatively coupled to each of the plurality of ophthalmic surgical machines and to each of the plurality of personal digital assistants, the central computer system further comprising a database of system profiles associated with each of the ophthalmic surgical machines, a database of technician profiles associated with each of the personal digital assistants, and a diagnostics engine configured to receive diagnostics data from the ophthalmic surgical machines, the diagnostics engine including a computer-based algorithm configured to:

detect an operation fault of at least one of the plurality of ophthalmic surgical machines based on the diagnostics data and the database of system profiles, the operation fault indicating a service requirement of the at least one of the plurality of ophthalmic surgical machines; and transmit an alert to at least one of the personal digital assistants using the database of technician profiles, the alert indicating the operation fault.

9. The ophthalmic surgical system of claim 8, wherein the central computer system is further programmed to send software upgrades to any of the ophthalmic surgical machines upon a request.

10. The ophthalmic surgical system of claim 8, wherein the plurality of remotely located ophthalmic surgical machines include one or more ophthalmic laser surgical machines, each producing an amount of total output energy during operation, and wherein the central computer system is configured to:

monitor the amount of total output energy of each of the one or more ophthalmic laser surgical machines; and notify at least one of the personal digital assistants when the amount of total output energy of one or more ophthalmic laser surgical machines exceeds a threshold energy level.

11. The ophthalmic surgical system of claim 10, wherein the central computer system is further configured to:

calculate a rate of change of the amount of total output energy for each of the one or more ophthalmic laser surgical machines; and notify at least one of the personal digital assistants when the rate of change of the amount of total output energy for one or more of the ophthalmic laser surgical machines exceeds a threshold rate.

12. The ophthalmic surgical system of claim 8, wherein one or more of the ophthalmic surgical machines are phacoemulsification machines each having a rotary vain pump, and wherein the central computer system is further configured to:

monitor a total usage of the rotary vain pump of each of the one or more phacoemulsification machines; and notify at least one of the personal digital assistants when the total usage of one of the rotary vain pumps exceeds a threshold value.

13. The ophthalmic surgical system of claim 8, wherein the central computer system is further configured to compare the data with the database of system profiles to predict the service requirement.

14. The ophthalmic surgical system of claim 8, wherein a first ophthalmic surgical machine comprises a plurality of components, wherein the central computer system is further configured to predict the service requirement of a first component of the plurality of components.

* * * * *